US009538985B2

(12) United States Patent
Mander et al.

(10) Patent No.: US 9,538,985 B2
(45) Date of Patent: Jan. 10, 2017

(54) HAND-HELD MEDICAL IMAGING SYSTEM WITH IMPROVED USER INTERFACE FOR DEPLOYING ON-SCREEN GRAPHICAL TOOLS AND ASSOCIATED APPARATUSES AND METHODS

(71) Applicant: FUJIFILM Sonosite, Inc., Bothell, WA (US)

(72) Inventors: Amanda Mander, Bainbridge Island, WA (US); Craig Chamberlain, Seattle, WA (US); Evan Mccormack, Kenmore, WA (US)

(*) Notice: Subject to any disclaimer, the term of this patent is extended or adjusted under 35 U.S.C. 154(b) by 202 days.

(21) Appl. No.: 14/256,744

(22) Filed: Apr. 18, 2014

(65) Prior Publication Data
US 2015/0297179 A1 Oct. 22, 2015

(51) Int. Cl.
| | |
|---|---|
| A61B 8/14 | (2006.01) |
| A61B 8/00 | (2006.01) |
| A61B 8/08 | (2006.01) |
| A61B 8/13 | (2006.01) |
| G06F 3/0488 | (2013.01) |
| G06F 3/0484 | (2013.01) |

(52) U.S. Cl.
CPC .............. *A61B 8/4427* (2013.01); *A61B 8/13* (2013.01); *A61B 8/463* (2013.01); *A61B 8/465* (2013.01); *A61B 8/467* (2013.01); *A61B 8/5207* (2013.01); *G06F 3/0488* (2013.01); *G06F 3/04842* (2013.01)

(58) Field of Classification Search
CPC ......... A61B 8/13; A61B 8/4427; A61B 8/463; A61B 8/465; A61B 8/467; A61B 8/5207; G06F 3/04842; G06F 3/0488; G06T 2207/10072; G06T 7/00
See application file for complete search history.

(56) References Cited

U.S. PATENT DOCUMENTS

2009/0043195 A1* 2/2009 Poland ................... A61B 8/00
600/437
2014/0098049 A1* 4/2014 Koch ..................... G06F 3/016
345/173

* cited by examiner

*Primary Examiner* — Mark Remaly (57) ABSTRACT

A portable ultrasound system having an enhanced user interface is disclosed herein. In one embodiment, a portable ultrasound system can include a hand-held base unit configured to present a graphical user interface that contains a first control area, a second control area, and an active image area. The first control area can have a number of graphical tools that can each be selectively activated by a user's finger. The second control area can include a control area having plurality of controls that can be selectively activated by the user's thumb to select a tool property of a number of tool properties associated with the selected one of the graphical tools. The active image area can display an ultrasound image, and the selected one of the graphical tools can be overlaid onto the image with the user-selected tool property.

11 Claims, 12 Drawing Sheets

HAND-HELD MEDICAL IMAGING SYSTEM WITH IMPROVED USER INTERFACE FOR DEPLOYING ON-SCREEN GRAPHICAL TOOLS AND ASSOCIATED APPARATUSES AND METHODS

TECHNICAL FIELD

The disclosed technology is related to medical imaging systems, and, in particular, some embodiments are related to portable ultrasound devices having a compact form factor and a user interface that facilitates hand-held operation.

BACKGROUND

Portable ultrasound imaging devices are used by anesthesiologists, emergency and critical care personnel, and other medical professionals. A portable ultrasound device can include a clamshell-type base unit having a handle for carrying the base unit. The base unit can fold open to a display and a keypad, and a user can connect an ultrasound transducer wand to the base unit to acquire and view ultrasound images on the display.

DETAILED DESCRIPTION

The following disclosure describes various types of hand-held imaging systems and associated apparatuses and methods. Certain details are set forth in the following description and FIGS. 1A-5F to provide a thorough understanding of various embodiments of the disclosed technology. Other details describing well-known structures and systems often associated with ultrasound systems, however, are not set forth below to avoid unnecessarily obscuring the description of the various embodiments of the disclosed technology.

Many of the details and features shown in the Figures are merely illustrative of particular embodiments of the disclosed technology. Accordingly, other embodiments can have other details and features without departing from the scope of the disclosed technology. In addition, those of ordinary skill in the art will understand that further embodiments can be practiced without several of the details described below. Furthermore, various embodiments of the technology can include structures other than those described and illustrated in the Figures. Moreover, the various elements and features illustrated in the Figures may not be drawn to scale.

In the Figures, identical reference numbers identify identical or at least generally similar elements. To facilitate the discussion of any particular element, the most significant digit or digits of any reference number refer to the Figure in which that element is first introduced. For example, element 110 is first introduced and discussed with reference to FIG. 1A.

Figure 1A:
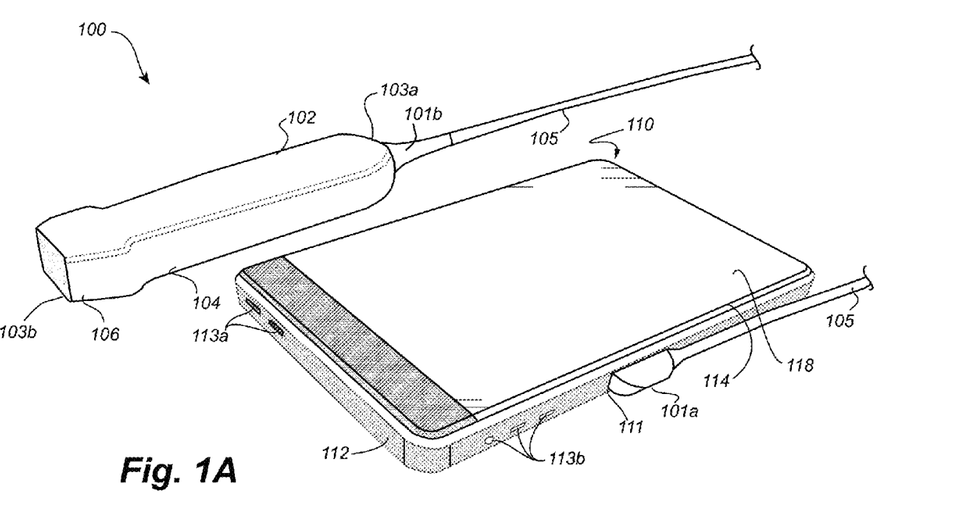
FIG. 1A is an isometric top view of a portable ultrasound system configured in accordance with an embodiment of the disclosed technology.

FIG. 1A is an isometric top view of a portable ultrasound imaging system 100 ("portable system 100") configured in accordance with an embodiment of the disclosed technology. Referring to FIG. 1A, the portable system 100 includes an ultrasound transducer device or a transducer wand 102 operably coupled to a hand-held base unit 110 ("base unit 110) by a signal cable 105. The signal cable 105 has a first end 101a and a second end 101b connected between a wand port 111 of the base unit 110 and a proximal end portion 103a of the transducer wand 102. In some embodiments, the signal cable 105 can include a connector or plug at the second end 101b (not shown) configured to removably couple the signal cable 105 to the transducer wand 102.

The transducer wand 102 includes a housing 104 (e.g., a molded plastic housing) extending from the proximal end portion 103a to a distal end portion 103b. The housing 104 includes a scan head region 106 that encloses a transducer array (not shown) within the housing 104 toward the distal end portion 103b. In some embodiments, the transducer wand 102 can include one or more buttons, triggers, or other input devices (not shown) configured, for example, to toggle power on or off, put the portable system 100 in a standby state, or to perform other operations. In other embodiments, the transducer wand 102 can include, for example, light-emitting elements that visually indicate an operational state of the transducer wand 102, a housing having a different shape and/or size, and/or other configurations or features.

In the illustrated embodiment, the base unit 110 includes a casing 112 (e.g., a plastic and/or metallic casing) and a touchscreen display 114 ("touchscreen 114") attached to the casing 112. The touchscreen 114 has a touchscreen surface 118 with transparent electrodes (e.g., indium tin oxide electrodes; not shown) in a capacitive configuration for sensing skin or stylus contact with the touchscreen surface 118. In another embodiment, the touchscreen surface 118 can include electrodes in a resistive configuration configured to sense pressure contact (rather than skin contact). In one aspect of this embodiment, a resistive configuration can enable a user to operate the touchscreen 114 with a gloved hand (e.g., a latex-gloved hand). The base unit 110 can also include user controls 113a and input/output (I/O) ports 113b at an outer edge of the base unit 110. The controls 113a can include, for example, buttons, knobs, switches, etc. The I/O ports 113b can include, for example, audio, universal serial bus (USB), high-definition multimedia interface (HDMI) ports), etc.

Figure 1B:
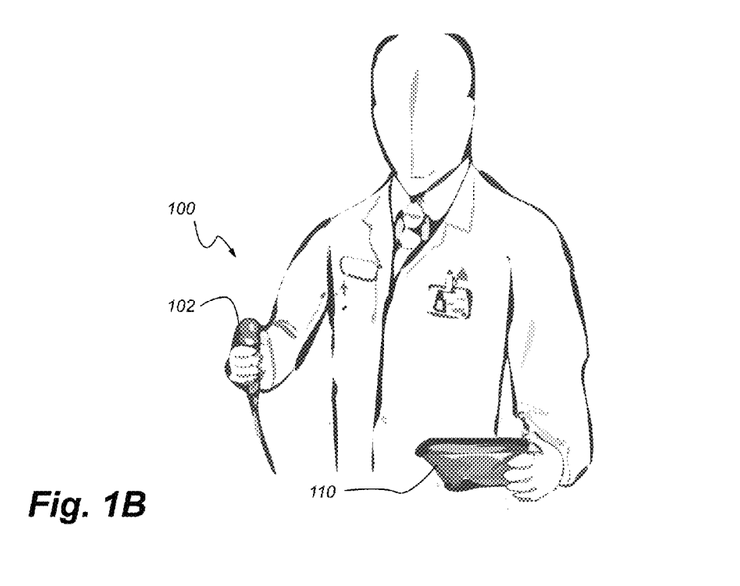
FIG. 1B shows a user carrying the portable ultrasound system of FIG. 1A in accordance with an embodiment of the disclosed technology.

FIG. 1B shows a user carrying the portable system 100 in accordance with an embodiment of the disclosed technology. In use, a physician or ultrasound technician can use the transducer wand 102 and the base unit 110 to perform an ultrasound scan. In particular, the user can place the transducer wand 102 toward a target region of interest within a patient (e.g., an organ and/or an internal cavity), and the base unit 110 displays an image on the touchscreen 114 (FIG. 1A) based on the ultrasound scan. In one aspect of this embodiment, a user can use one hand (e.g., the right hand) to operate the transducer wand 102 and simultaneously use the other hand (e.g., the left hand) to carry and operate the base unit 110. In one embodiment described in greater detail below with reference to FIGS. 3A-3G, the touchscreen 114 can include a graphical thumb controller (not visible in FIG. 1B) configured to control the base unit 110. In another embodiment described in greater detail below with reference to FIG. 5, the portably system can include a harness, belt, or other wearable feature that allow a user to operate the system while simultaneously carrying it on their person.

Figure 2:
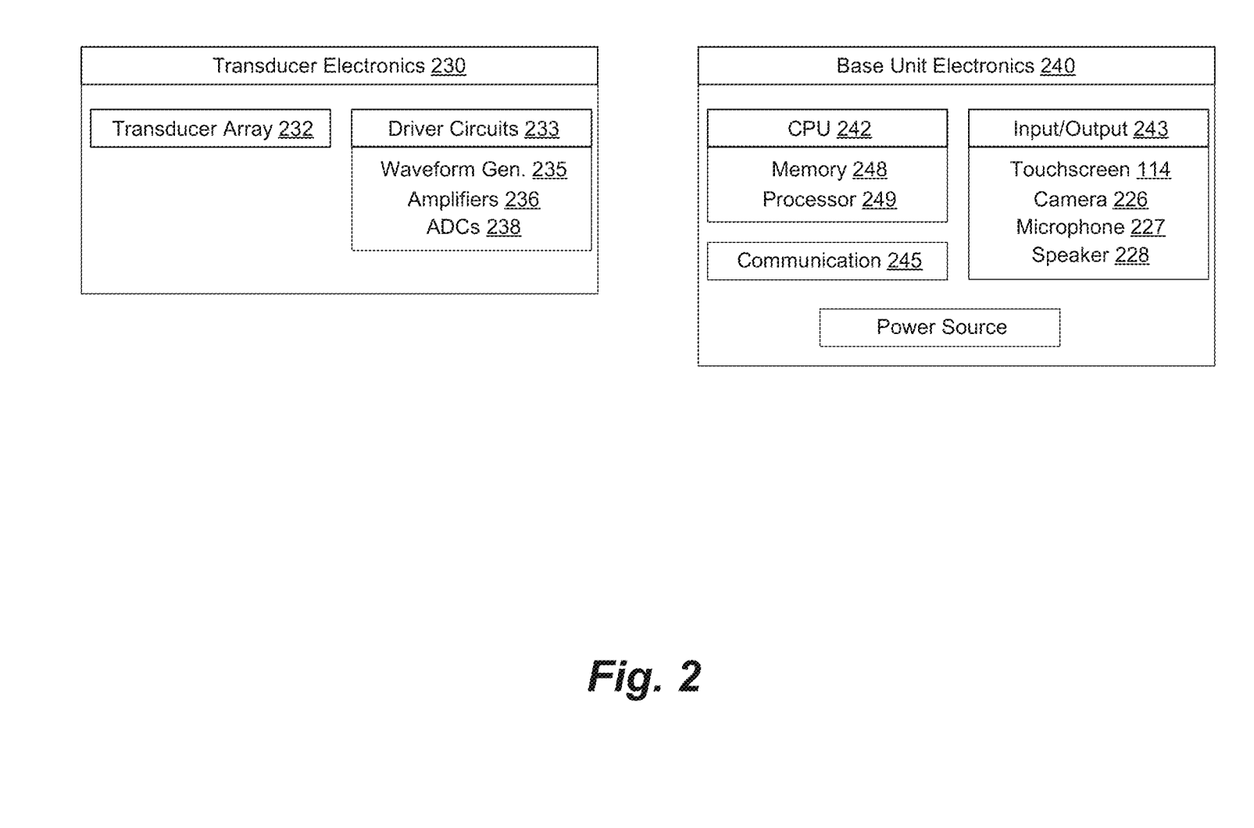
FIG. 2 is a schematic diagram of various electronic components of the portable system configured in accordance with an embodiment of the disclosed technology.

FIG. 2 is a schematic diagram of various electronic components of the portable system 100 configured in accordance with an embodiment of the disclosed technology. Referring first to FIG. 2, the portable system 100 includes transducer electronics 230 at the transducer wand 102 (FIG. 1A) and base-unit electronics 240 at the base unit 110 (FIG. 1A). The transducer electronics 230 can drive a transducer array 232, such as an array of microelectromechanical transducer elements, located at the scan head region 106 (FIG. 1A). The transducer electronics 230 can also include one or more driver circuits 233 configured to operate the transducer array 232. The driver circuits 233 can include, for example, waveform generators 235, amplifiers 236, analog to digital converts (ADCs) 238, and other ultrasound signal processing components (e.g., a CPU, controller, transmit/receive beam former circuitry, etc.). In some embodiments, at least a portion of the driver circuits 233 can be located at the base unit 110.

The base-unit electronics 240 include a CPU 242, input/out devices 243, and communication components 245. The CPU 242 includes a programmable processor 249 configured to execute instructions in memory 248 in order to perform various processes, logic flows, and routines. The input/out devices 243 can include, for example, the touchscreen 114, a camera 226, a microphone 227, and/or a speaker 228. The communication components 245 can include, for example, signal buses coupled to the wand port 111, the input controls 113a, the communication ports 113b, and the touchscreen 114. In several embodiments, the communication components 245 can further include a network adaptor, a wireless transceiver (e.g., Wi-Fi or cellular transceiver), or other suitable components for communication over the Internet, a computer network, and/or a wireless network.

In operation, the driver circuits 233 can operate the transducer array 232 to produce and steer an acoustic signal toward a target region of interest. The base-unit electronics 240, in turn, can drive the driver circuits 233 based on user input. For example, as described in greater detail below, the user can provide input by operating various graphical controls presented at the touchscreen 114. The driver circuits 233 can also produce information based on the acoustic signals returned to the transducer array 232, which the base-unit electronics 240 uses to display ultrasound images on the touchscreen 114 as the information is acquired.

Figure 3A:
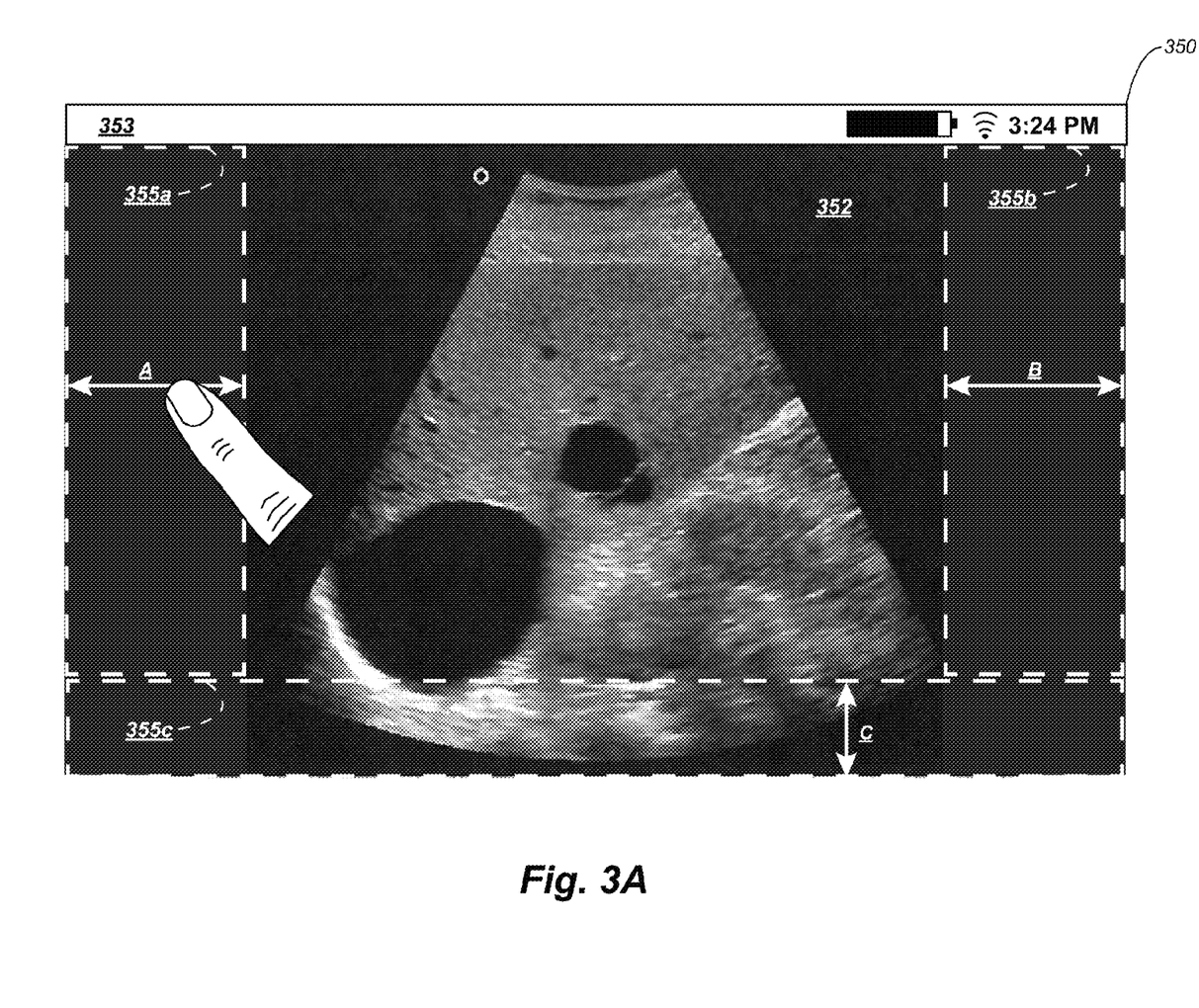
FIGS. 3A-3G show a graphical user interface presented at a touchscreen of a portable ultrasound system in accordance with several embodiments of the disclosed technology.

FIGS. 3A-3G show a graphical user interface 350 presented at the touchscreen 114 (FIG. 1A) in various display states in accordance with several embodiments of the disclosed technology. Referring first to FIG. 3A, the graphical user interface 350 includes an active image area 352 in which an ultrasound image is displayed, a status bar 353 (indicating the current time, a wireless signal strength, battery lifetime, etc.), and three control areas 355a-c (shown in silhouette form in FIG. 3A). In use, the control areas 355 can be expanded from a retracted state (as shown) such that they overlay portions of the active image area 352. For example, in several embodiments the user can slide a finger across the touchscreen 114 in the general directions shown by arrows A-C to expand/contract the three control areas 355a-c, respectively. As described in greater detail below, when expanded, the control areas 355 can present various graphical tools (e.g., markers, labels, calipers, etc.) that the user can position or overlay onto the active image area 352 (e.g., by dragging the graphical tool onto the active image area 352). In some embodiments, the control areas 355 can automatically retract if the user does not touch or access the selected control area for a certain period of time (e.g., within several seconds of not touching the selected control area).

Figure 3B:
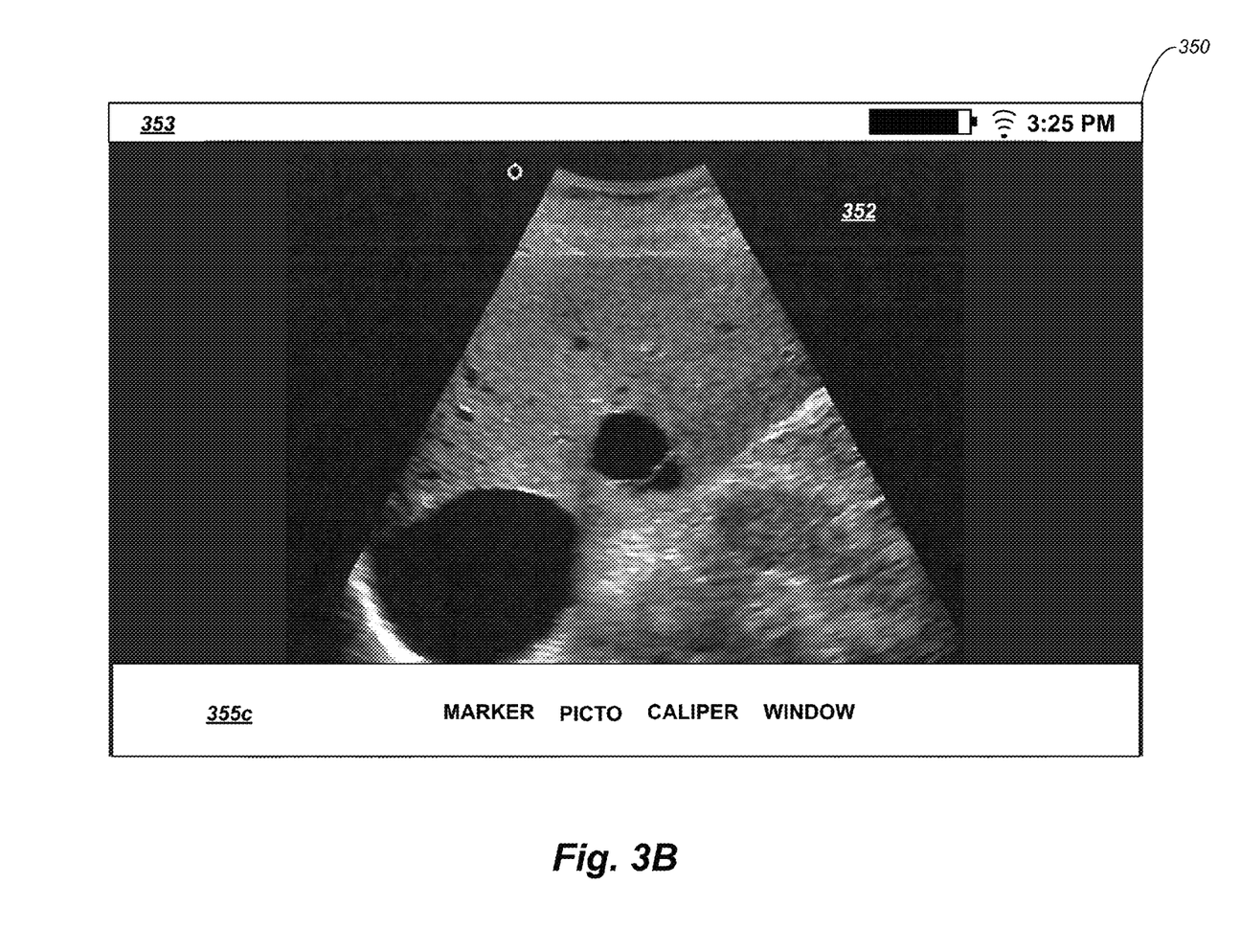

FIG. 3B shows the graphical user interface 350 in a configuration in which the user has expanded the third control area 355c. As shown, the third control area 355c includes touch-selectable features, or soft buttons, corresponding to a number of graphical tools the user can overlay or implement on an ultrasound image or a series of ultrasound images displayed at the active image area 352. In general, such graphical tools can identify, label, measure, or otherwise help a user evaluate an ultrasound image. For example, the "MARKER" and "PICTO" soft buttons can be selected to overlay a graphical marker or a pictograph, respectively, on the ultrasound image, the "CALIPER" soft button can be selected to measure a distance between objects captured in the ultrasound image, and the "WINDOW" soft button tool can be selected by the user to zoom and/or pan the image.

Figure 3C:
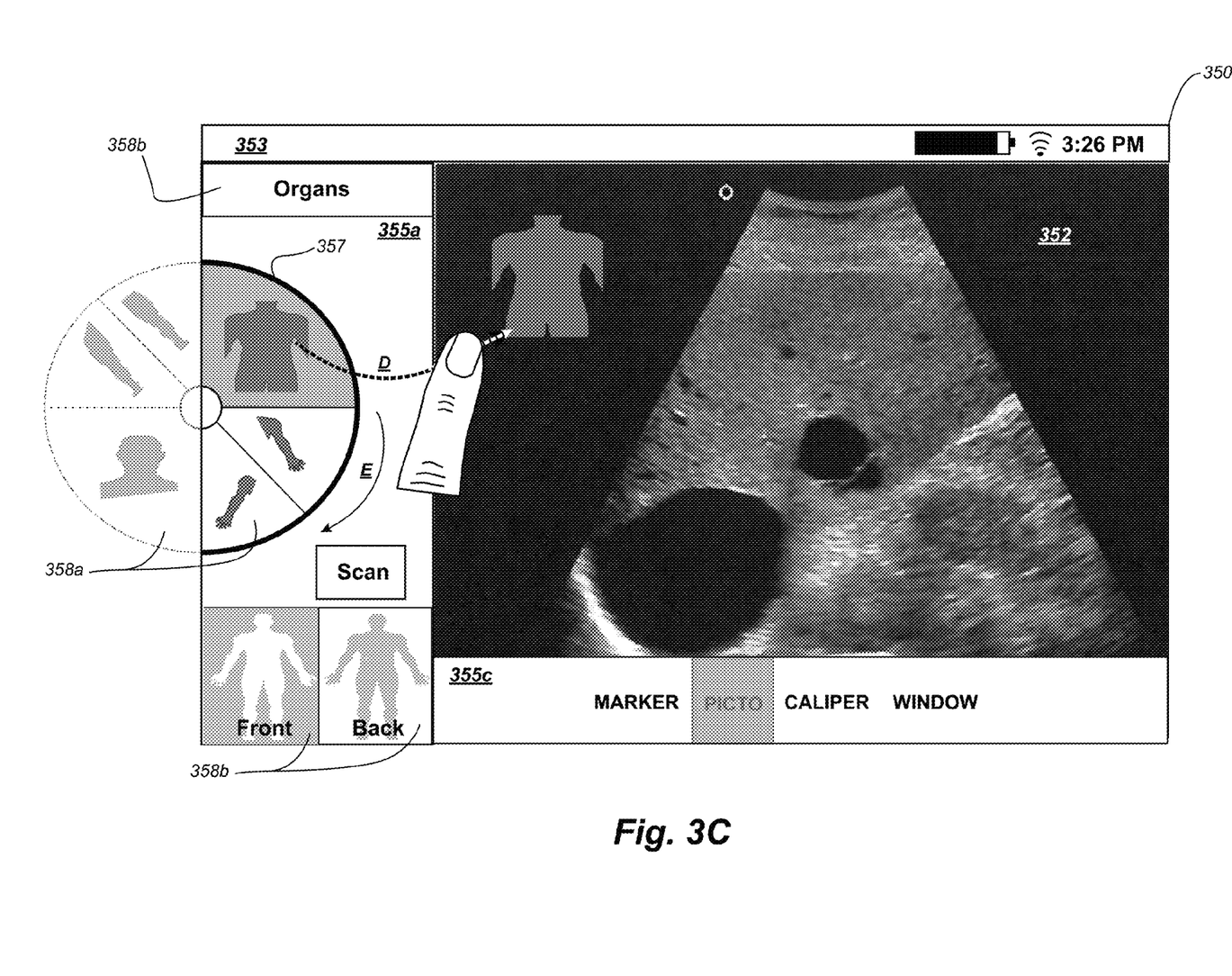

FIG. 3C shows the graphical user interface 350 in a configuration in which the user has selected the "PICTO" soft button in the thumbwheel 357. In response to this selection, the processor opens the first control area 355a. As shown, the first control area 355a includes a thumbwheel 357, soft button controls 358a that are on the thumbwheel 357, and one or more other soft button controls 358b that are off the thumbwheel 357. In one aspect of this embodiment, the soft button controls 358a on the thumbwheel 357 enable users to select a tool attribute or tool property of the selected graphical tool, such as its visual or graphical appearance. For example, when the user selects the "PICTO" button, the soft buttons 358a on the thumbwheel 357 each correspond to a graphical icon representing an anatomical location (e.g., a torso region, a head region, a left-arm region, etc.). Also, the user can select the "Front" or "Back" icons to further indicate from which side of the patient the ultrasound image was acquired. In another embodiment, the touch-selectable controls can be selected to perform other functions. For example, the "SCAN" soft button can be selected to initiate an ultrasound scan. In these and other embodiments, the touch-selectable controls can include controls described, for example, in co-pending U.S. patent application Ser. No. 14/256,759, titled "Hand-Held Medical Imaging System with Thumb Controller and Associated Apparatuses and Methods" filed concurrently herewith and incorporated herein in its entirety by reference. In another embodiment, the control area 368 includes touch-selectable features that do not modify ultrasound scanning parameters. For example, the user can select the "Marker" soft button to position a graphical marker on the ultrasound image.

Upon selecting a tool property from the thumbwheel 357, the user can position (e.g., slide or drag) the pictograph on the active image area 352 (as shown by arrow D). For example, in the illustrated embodiment the user has dragged the pictograph representing the human torso onto the active image area 352. In one aspect of this embodiment, the thumbwheel 357 allows the user to access other soft buttons not in view on the touchscreen 114. For example, users can use their thumb to sweep over the soft buttons displayed in order to rotate the thumbwheel 357 in the clockwise direction (as shown, e.g., by Arrow E) to hide one or more of the displayed soft buttons and bring other soft buttons into view. In another embodiment, users can rotate the thumbwheel 357 by touching the thumbwheel 357 at its outer edge or periphery (i.e., via the touchscreen 114) and then spinning the thumbwheel 357 until a desired soft button comes into view.

Figure 3D:
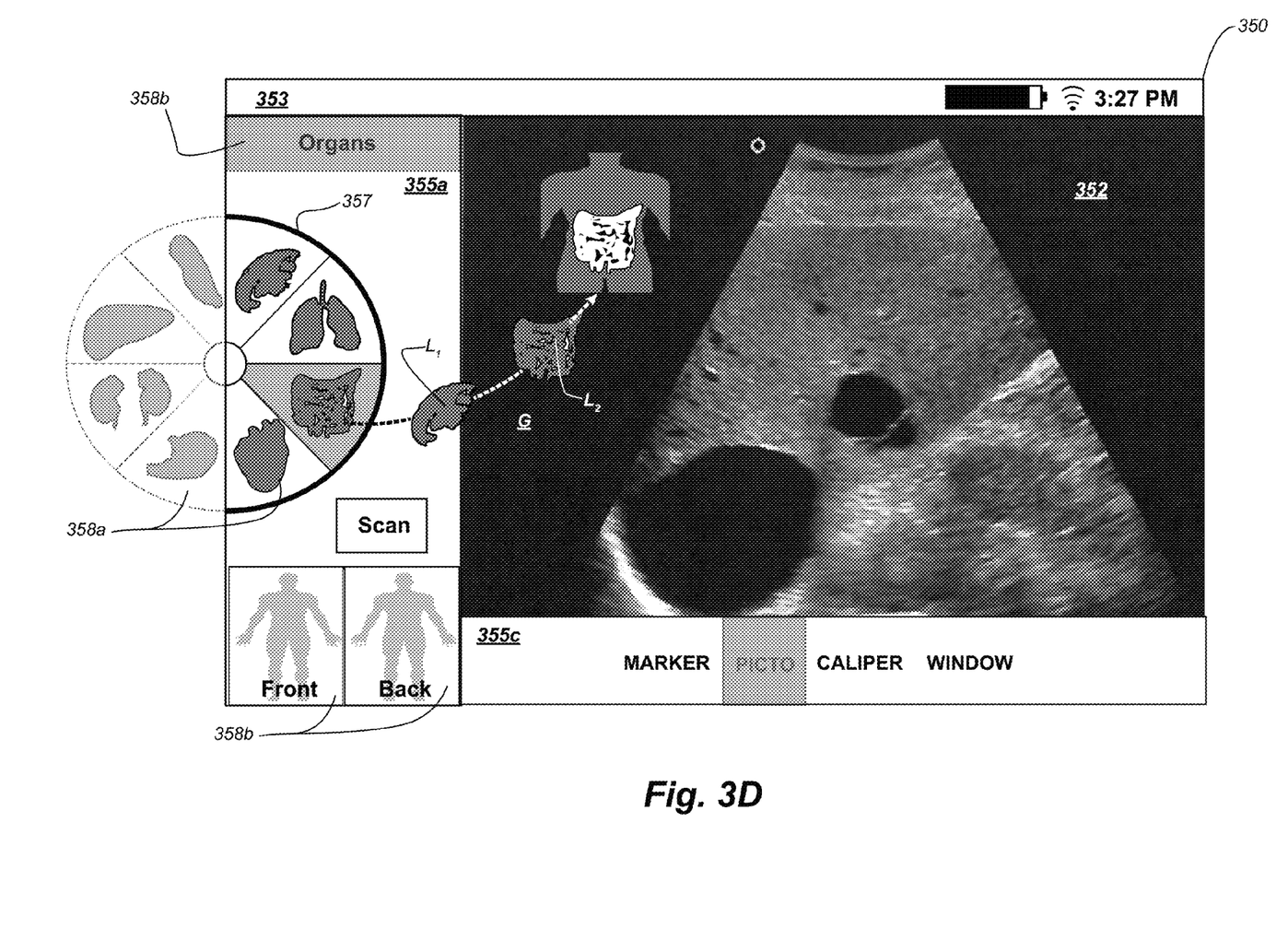

FIG. 3D shows the graphical user interface 350 in a configuration in which the user has selected the "Organs" button within the first control region 355a. In response, the thumbwheel 357 has presented touch-selectable icons that each represent an organ within the human body. In the illustrated embodiment, the user has selected an icon representing the lower intestinal tract and dragged this icon (as shown by arrow G) onto the human torso icon previously place on the active image area 352. In one aspect of this embodiment, users can dynamically select the display state of the selected pictograph with their thumb using the thumbwheel 357 while simultaneously dragging a pictograph onto the active image area 352 with their finger. For example, as shown in FIG. 3D, the user initially selected the brain icon from the thumbwheel 357. As the user dragged the brain icon from the thumbwheel to location $L_1$ on the path of the arrow G, the user simultaneously operated the thumbwheel 357 such that by the time the user's finger reached location $L_2$, the icon representing the lower intestinal tract was displayed on the active image area 352.

Figure 3E:
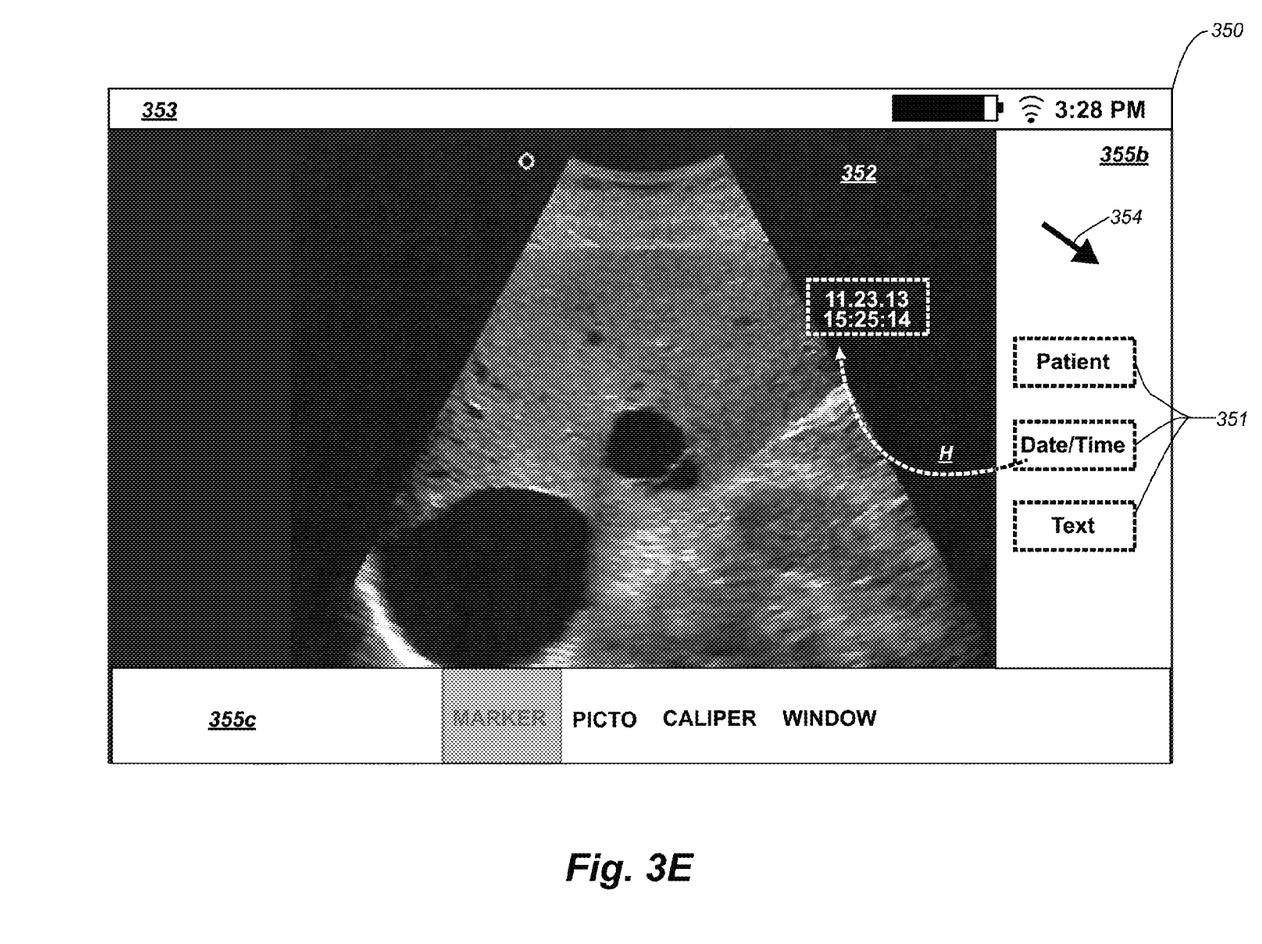

FIG. 3E shows the graphical user interface 350 in a configuration in which the user has selected the "Marker" button within the third control area 355c. In response to selecting the "Marker" button, the processor has displayed various graphical markers in the second control area 355b. In particular, the processor has displayed textual markers 351 and an arrow marker 354 that the user can drag onto the image at the active image area 352. As shown, the user has selected a "Date/Stamp" icon and dragged this icon from the second control area 355b onto the image at the active image area 352. The user can also select a "Text" icon to select a textual marker that allows the user to annotate text onto the image (e.g., via a pop-up graphical keyboard; not shown). In yet another embodiment, the textual marker can include a textual label selected from a library of labels (not shown) corresponding to, e.g., a particular portion of the anatomy or a pathology.

Figure 3F:
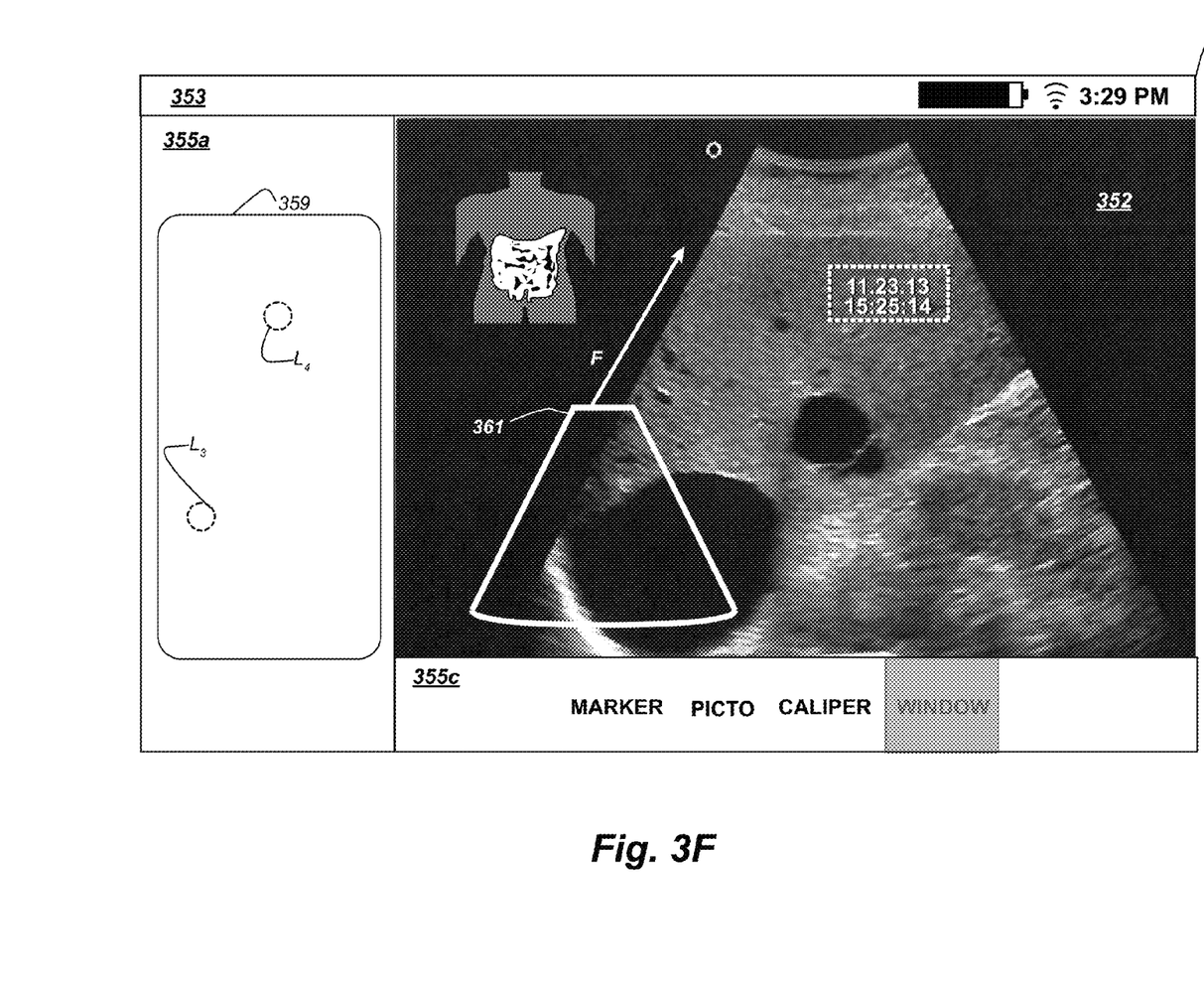

FIG. 3F shows the graphical user interface 350 in a configuration in which the user has selected the "Window" button in the third control area 355c. As shown, the processor has presented a window 361 on the image at the active image area 352 and a track pad 359 in the first control area 355a. In one aspect of this embodiment, the user can use the track pad 359 to move the window 361 to various locations on the active image area 352. For example, a user can swipe a finger or thumb from location $L_3$ to location $L_4$ on the track pad to move the window 361 in the direction of arrow F on the active image area 352. In some embodiments, the user can make certain swiping gestures with the thumb or finger across the track pad 359 to zoom into an image or, conversely, to zoom away from an image. For example, in one embodiment a generally inward pinching motion can zoom into an image. In another embodiment, the track pad 359 can also enable fine grain placement of a graphical tool. For example, a user may use the track pad 359 for fine grain placement of the arrow graphical marker 354 shown in FIG. 3E.

Figure 3G:
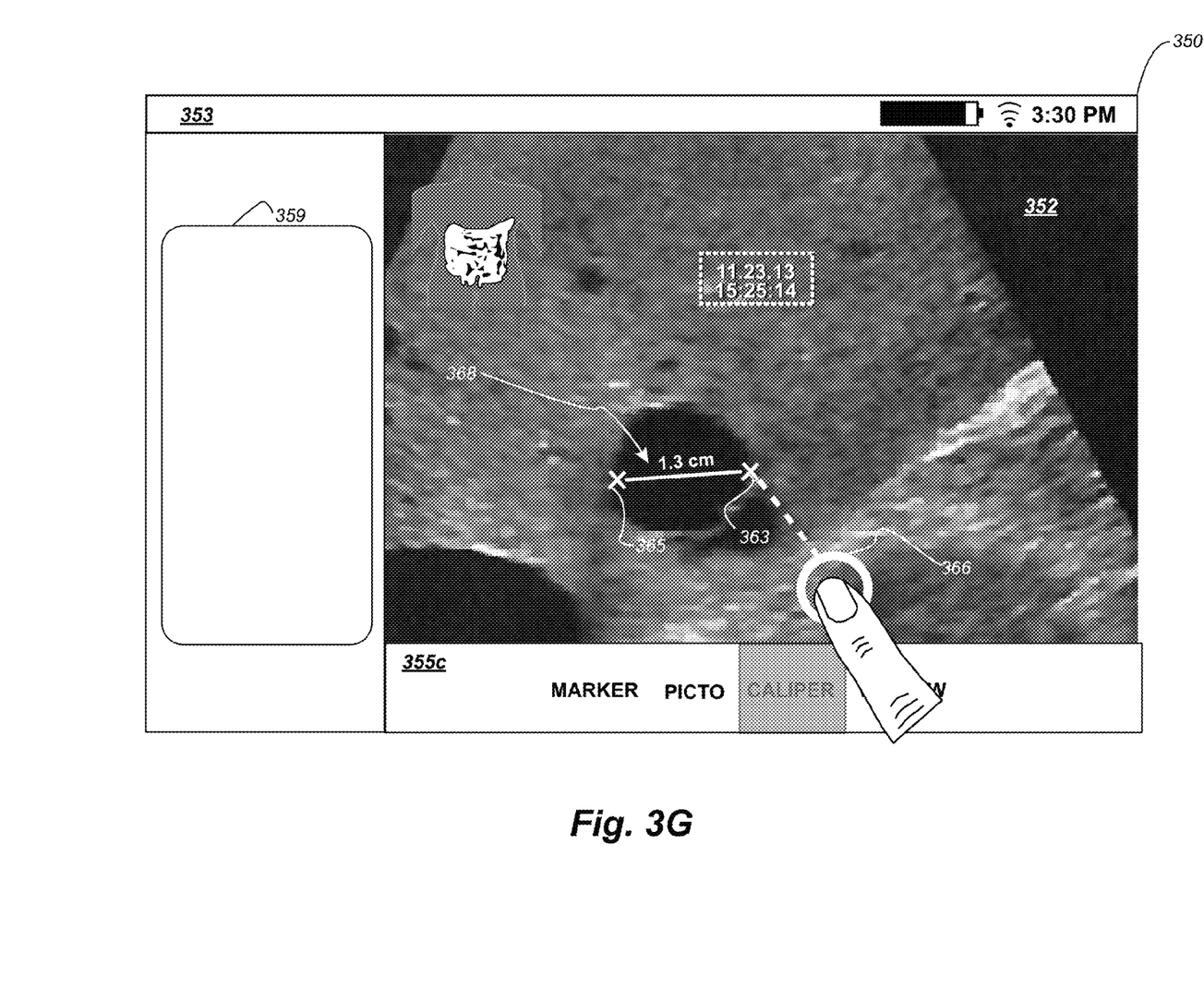

FIG. 3G shows the graphical user interface 350 in a configuration in which the user has selected to overlay a graphical caliper tool 368 on the ultrasound image. As shown, the user has selected the "Caliper" soft button of the third control area 355c. The processor then produces a display of a measurement (e.g., 1.0 cm) between a pair of endpoints 363, 365. If the user touches the display near either endpoint, the processor produces a handle 366 that is connected by a dotted line to the nearest endpoint that was touched. Then user can than move endpoint by dragging the handle 366 in the direction where the endpoint is to move. In one aspect of this embodiment, the user can use the graphical handle 366 to change the location of the end point 363 on the active image area 352 (e.g., by dragging the graphical handle 366 to a different location on the active image area 352). As the user changes the location, the measurement taken by the caliper tool 368 changes based on the new position of the end point 363 relative to the other endpoint 365 of the caliper tool 368. In another aspect of this embodiment, the graphical handle 366 is displayed such that it is offset from the endpoint 363. As such, the user's fingertip does not obscure the user's view of the endpoint 363 while operating the graphical caliper tool 368.

Figure 4:
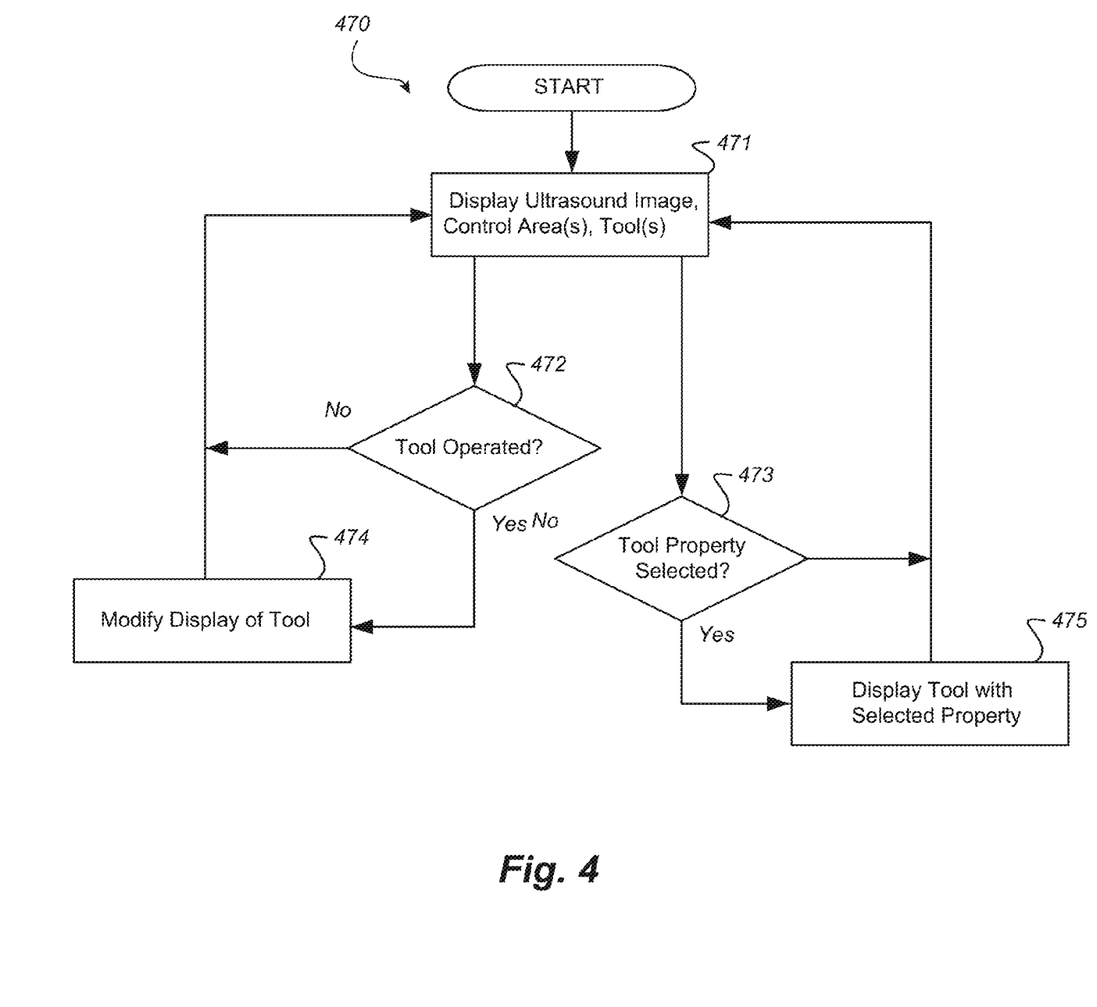
FIG. 4 is a flow diagram illustrating a routine for providing on-screen graphical tools in a portable ultrasound system in accordance with an embodiment of the disclosed technology.

FIG. 4 is a flow diagram illustrating a routine 470 for providing on-screen graphical tools in a portable ultrasound system in accordance with an embodiment of the disclosed technology. The routine 470 begins at block 471 by displaying an ultrasound image in the active image area 352 as well as any control areas 355 and/or graphical tools that have been previously selected by the user. The routine 470 can also display user-selectable tool properties associated with a particular one of the graphical tools (e.g., anatomical locations to be represented by a pictograph). Upon displaying the active image area 352 and any user-selected graphical tools, the routine 470 proceeds to block 472 to detect whether the user has operated a graphical tool (e.g., by dragging a pictograph from the third control area 355c onto the active image area 352 with the user's index finger). At the same time, the routine 472 can also proceed to block 473 to detect whether the user has selected a tool property (e.g., by selecting a pictograph attribute with the user's thumb).

At block 472, the routine 470 detects whether a user has operated a graphical tool. For example, the routine 470 can detect whether a user has selected the "PICTO" soft button to place a pictograph on the active image area 352. The routine 470 also detects any movement associated with the selected graphical tool. For example, the routine 470 can detect whether the user has dragged a graphical tool from the third control area 355c and onto the active image area 352. The routine 470 can also detect movement or motion on the track pad 359 for placement or positioning of a window, a marker, a caliper, or other tool. If the routine 470 has detected the operation of the graphical tool, the routine 470 proceeds to block 474 to modify the display of the graphical tool based on the detected selection and/or motion associated with the graphical tool before returning again to block 471. Otherwise, the routine 470 can proceed directly to block 471 to continue displaying the ultrasound image and any graphical tools previously selected by the user.

At block 473, the routine 470 detects whether the user has selected a tool property. For example, the routine can detect whether the user has rotated the thumbwheel 357 and/or selected a control on the thumbwheel 357 corresponding to a particular tool property. In several embodiments, the user can modify the tool property at the same as the user is operating the graphical tool at block 472. For example, the routine can detect operation of the thumbwheel 357 at the same time that the user is moving a graphical marker onto the active image area 352, as discussed above. Once the routine 470 has detected the selection of a tool property, the routine 470 proceeds to block 475 to display the graphical tool with the selected tool property before returning again to block 471. Otherwise, the routine 470 proceeds directly to block 471 to continuing displaying the ultrasound image and any graphical tools previously selected by the user.

As discussed above, in several embodiments, the user can employ a wearable support system that allows users to carry the portable system 100 directly on their person. For example, FIGS. 5A-5F show portable device support systems configured in various embodiments of the disclosed technology. Referring to FIGS. 5A-25, in several embodiments a support system 590a (FIG. 5A) can include a belt 592 that allows the user to carry the base unit 110 at the user's waist. In some embodiments, a support system 590b (FIG. 5B) can include a sling 593 that supports the weight of the base unit 110 over the user's shoulder and at the user's waist. In one aspect of this embodiment, the sling 593 has loops 594, eyelets, or other features through which the signal cable 105 can be routed on the sling 593, over the user's shoulder, and around the user's neck. As shown, this allows the user to drape the signal cable 105 over the other shoulder for carrying the transducer wand 102 when not in use. In another embodiment, a support system 590c (FIG. 5C) can include a harness 596 that the user can carry on their shoulders and/or neck. In one aspect of this embodiment, the harness 596 can hold the base unit 110 at a viewing angle that allows users to view the display on base unit 110 without having to hold the base unit 110 with their hand.

Figure 5A:
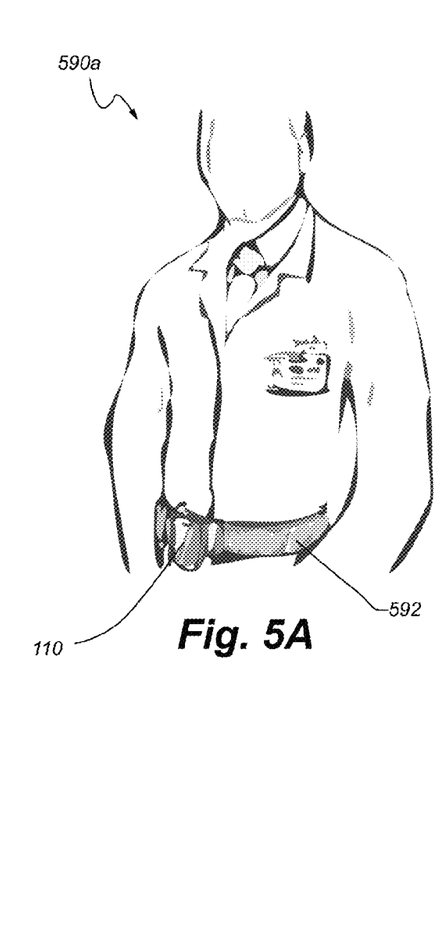
FIGS. 5A-5F show portable device support systems configured in accordance with various embodiments of the disclosed technology.
Figure 5B:
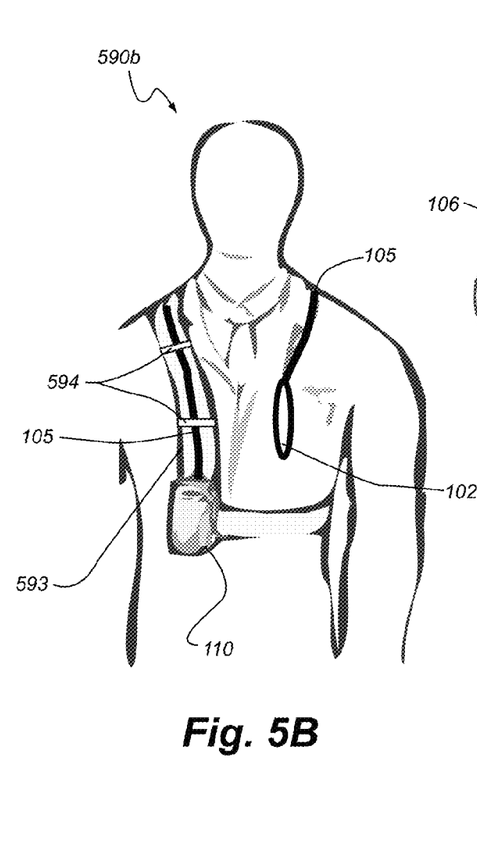
Figure 5C:
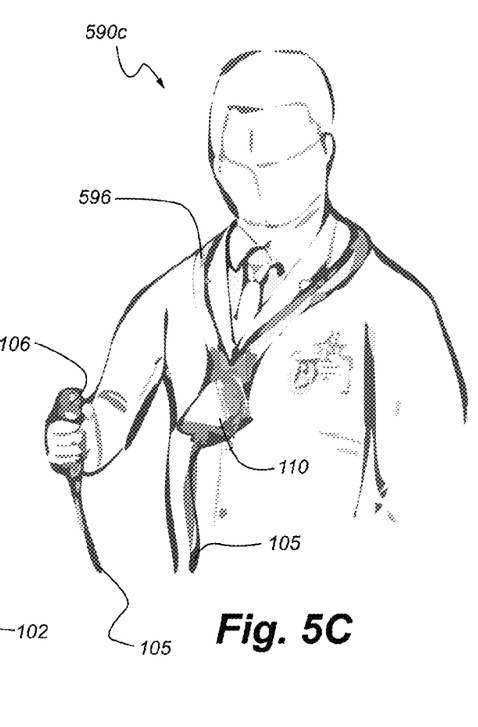
Figures 5D, 5E, 5F:
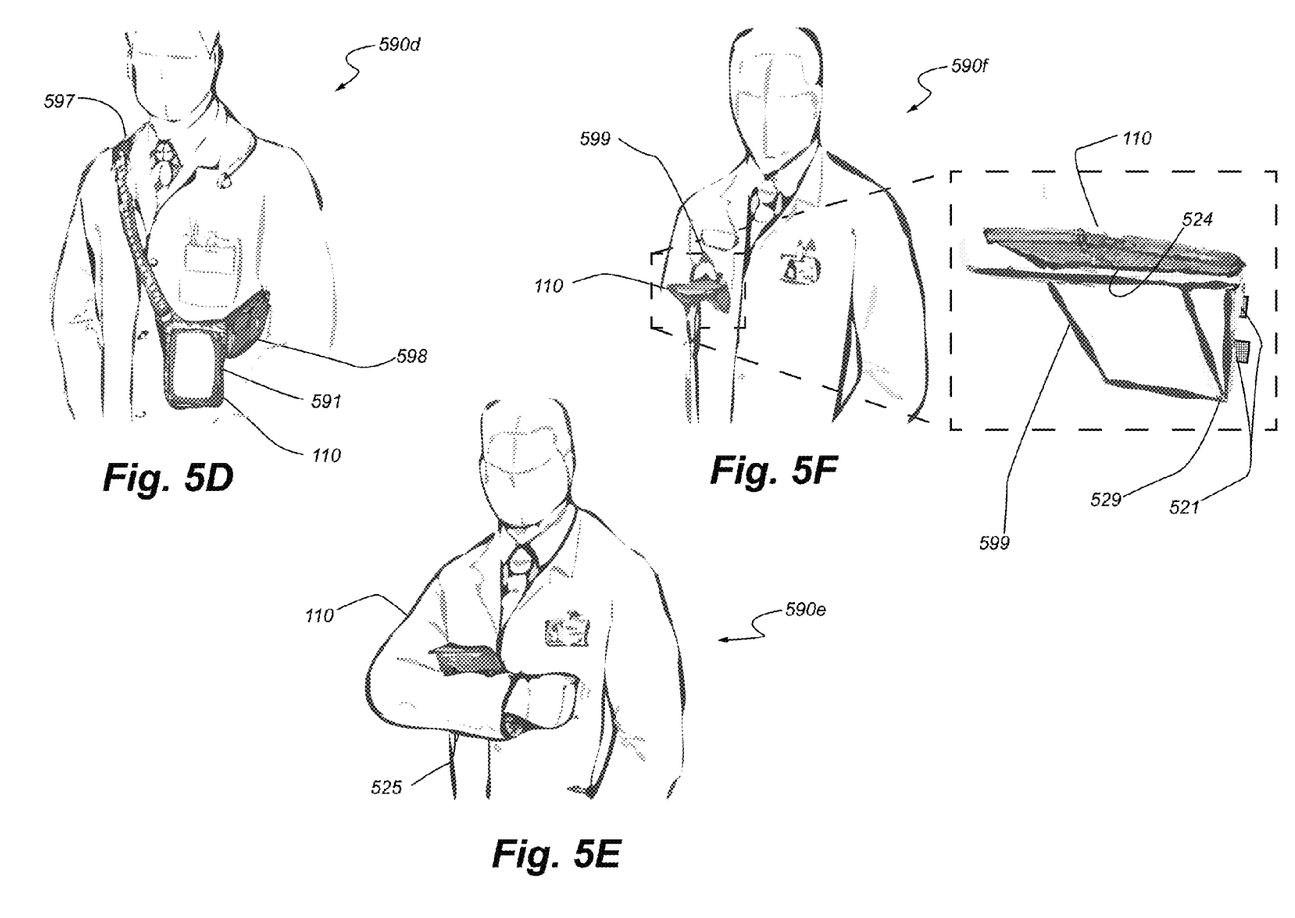

Referring to FIGS. 5D-5F, in one embodiment a support system 590d (FIG. 5D) can include a holster 591 (e.g., a hard-plastic protective holster) carried by a sling 597. As shown, the sling 597 can include individual pockets or compartments 598 for storing components, such as spare batteries and/or the transducer wand 102. In certain embodiments, a support system 590e (FIG. 5E) can include attachment features 525 (e.g., clips, snaps, etc.) that can attach the base unit 110 to a user's sleeve or a wrist band (not shown). In one embodiment, a support system 550f (FIG. 5F) can include a foldable platform 599 formed from, e.g., a rigid plastic material, reinforced leather, or other suitable material that can attach to a backside surface 524 of the base unit 110. In one aspect of this embodiment, the foldable platform 599 can include a panel 529 that attaches to a user's clothing via attachment features 521, such as a hook/loop type of fastener, magnets, or the like. Similar to the harness 596 (FIG. 5C), the foldable platform 599 includes an angled support that holds the base unit 110 at a viewing angle that allows users to view the display on base unit 110 without having to hold the base unit 110 with their hand.

From the foregoing, it will be appreciated that specific embodiments of the disclosed technology have been described herein for purposes of illustration, but that various modifications may be made without deviating from the scope of the various embodiments of the disclosed technology. Moreover, because many of the basic structures and functions of transducer arrays, transducer electronics, and other processor electronics are known, they have not been shown or described in further detail to avoid unnecessarily obscuring the described embodiments. Further, while various advantages and features associated with certain embodiments of the disclosed technology have been described above in the context of those embodiments, other embodiments may also exhibit such advantages and/or features, and not all embodiments need necessarily exhibit such advantages and/or features to fall within the scope of the disclosed technology.

The invention claimed is:

1. A portable ultrasound system, comprising a hand-held base unit that includes:
   a touchscreen display; and
   a programmable processor configured to execute instructions that cause the processor to produce a display on the touchscreen display, including—
      a first control area having a number of graphical tools that can each be selectively activated by a user,
      a second control area that is accessible by a hand of the user that is holding the portable ultrasound system, wherein the second control area includes a plurality of controls that can be selectively activated by a thumb of the user to select an attribute of a selected graphical tool, and
      an active image area in which an image of a patient obtained from an ultrasound scan is displayed and at which the selected one of the graphical tools can be overlaid onto the image with the user-selected tool attribute.

2. The portable ultrasound system of claim 1 wherein:
   one of the graphical tools that can be selected is a pictograph; and
   the second control area includes a control to select an attribute indicative of a region of the human anatomy.

3. The portable ultrasound system of claim 1 wherein the processor is configured to execute instructions to:
   display a selected graphical tool at a first location in the first control area or the second control area;
   detect movement of a user's finger from a first location to a second location in the active image area; and
   overlay the selected one of the graphical tools at a second location in the active image area in response to the detected movement.

4. The portable ultrasound system of claim 1 wherein the processor is configured to execute further instructions to:
   detect movement of a user's finger along a path that extends between a first location in the first control area and a second location in the active image area;
   detect a first selection of a first control in the second control area corresponding to an attribute of the selected graphical tool;
   display the selected graphical tool with the selected attribute at a first location on the path;
   detect a second selection in the second control area corresponding to a second attribute of the graphical tool; and
   display the selected graphical tool with the second attribute at a second location on the path different than the first location.

5. The portable ultrasound system of claim 2 wherein the processor is configured to execute further instructions, in order to:
   display a thumbwheel in the second control area that contains the controls;
   detect movement of the user's thumb corresponding to rotation of the thumbwheel; and
   move individual controls onto and off of the second control area in response to the detected movement of the user's thumb.

6. A portable, hand-held ultrasound system, comprising:
   a housing having a touchscreen display, wherein the housing is configured to be held in an operator's hand at a first end portion of the housing;

one or more processors; and a memory configured to store instructions that, when executed by the processor, cause the processor to— output a control area on the touchscreen display at the first end portion of the housing, the control area having a first display state and at least a second, different display state, wherein the control area in the first display state includes a plurality of icons each having graphical representations depicting corresponding exterior portions of a subject's anatomy;

output an active image area in a center portion of the touchscreen display, wherein the active image area includes a medical image of a region of interest in a portion of the subject's anatomy; and output a first one of the plurality of icons overlaid on the active image area, wherein the exterior portion of the subject's anatomy depicted in the graphical representation on the first one of the plurality of icons generally corresponds to the portion of the subject's anatomy that includes the region of interest in the medical image.

7. The portable, hand-held ultrasound system of claim 6 wherein:

the instructions stored on the memory further include instructions that, when executed by the processor, cause the processor to output the control area in the second display state; and the control area in the second display state includes a plurality of second icons each having graphical representations depicting corresponding interior organs of the subject's anatomy.

8. The portable, hand-held ultrasound system of claim 7 wherein:

the plurality of icons is a plurality of first icons;

the first one of the plurality of icons is a first one of the plurality of first icons; and the instructions stored on the memory further include instructions that, when executed by the processor, cause the processor to output a first one of the plurality of second icons in the active image area and overlaid on the first one of the plurality of first icons, wherein the interior organ of the subject's anatomy depicted in the graphical representation on the first one of the plurality of second icons generally corresponds to an organ in the subject's anatomy that includes the region of interest in the medical image.

9. The portable, hand-held ultrasound system of claim 7 wherein:

the plurality of icons is a plurality of first icons;

the first one of the plurality of icons is a first one of the plurality of first icons; and the instructions stored on the memory further include instructions that, when executed by the processor, cause the processor to output only selected ones of the plurality of second icons depicting interior organs from the portion of the subject's anatomy depicted in the first one of the plurality of first icons.

10. The portable, hand-held ultrasound system of claim 6, further comprising:

a cable having a first end removably attached to the housing, and a second end; and a medical imaging probe attached to the second end of the cable.

11. The portable, hand-held ultrasound system of claim 10 wherein the instructions stored on the memory further include instructions that, when executed by the processor, cause the processor to operate in a standby state in response to input received at the medical imaging probe.

* * * * *